US005409908A

United States Patent [19]

Sanchez et al.

[11] Patent Number: 5,409,908

[45] Date of Patent: Apr. 25, 1995

[54] COMPLEXING URUSHIOLS

[75] Inventors: Robert A. Sanchez, Carlsbad; Sheldon S. Hendler, La Jolla, both of Calif.

[73] Assignee: Vyrex Corporation, La Jolla, Calif.

[21] Appl. No.: 138,215

[22] Filed: Oct. 20, 1993

[51] Int. Cl.[6] .......... A61K 31/715
[52] U.S. Cl. .......... 514/58; 514/54
[58] Field of Search .......... 514/54, 58

[56] References Cited

U.S. PATENT DOCUMENTS

| | | | |
|---|---|---|---|
| 3,875,301 | 4/1975 | Windheuser | 424/45 |
| 4,352,794 | 10/1982 | Koch | 536/103 |
| 4,727,064 | 2/1988 | Pitha | 514/58 |
| 4,808,232 | 2/1989 | Beesley | 514/58 |
| 5,296,472 | 3/1994 | Sanchez et al. | 514/58 |

*Primary Examiner*—Richard L. Raymond
*Assistant Examiner*—Scott C. Rand
*Attorney, Agent, or Firm*—Glenna Hendricks; Stephen Gates

[57] ABSTRACT

This invention relates to use of cyclodextrins to complex urushiols to protect against and to treat irritation arising from exposure to urushiols. Cyclodextrins, particularly gamma-cyclodextrins, are capable of binding strongly to urushiols and can be used effectively to prevent irritation of tissue that is exposed to urushiols.

Cyclodextrin-urushiol complexes can also be used to desensitize against urushiol. Compositions containing cyclodextrin/urushiol complexes may be provided as tablets for buccal administration in dosages sufficient to induce desensitizing response.

7 Claims, No Drawings

COMPLEXING URUSHIOLS

FIELD OF THE INVENTION

This invention relates to use of cyclodextrins to complex urushiols to protect against and to treat irritation arising from exposure to urushiols.

BACKGROUND OF THE INVENTION

Urushiols are a group of alkylcatechols produced by plants which cause mild to severe allergenic responses. These substances are produced by plants, including but not limited to the genus Rhus, which includes poison ivy, poison oak and poison sumac. Exposure to the plant causes oily urushiols to be transferred to the skin. The result is painful contact dermatitis followed, at times, by infection. The viscous oils are water-insoluble and are washed off only with difficulty. The attempt to clean the skin of the urushiols often results in further spreading of the urushiols resulting in increased irritation and discomfort. In some instances, burning of the plants causes the urushiols to be discharged into the air and carried on the wind. In such instances, not only the skin and mucous membranes, but also the lungs may be affected by exposure to the urushiols.

Protective clothing has often been worn as a means of prevention. Treatment has usually consisted of application of steroid preparations and of soothing lotions such as Calamine lotion. None of these treatments have provided particularly satisfactory results.

Attempts to desensitize susceptible persons by administration of urushiols by mouth have proven disappointing. Part of the problem is that the allergenic urushiol liquid dosage forms are inherently hard to handle. The frequent side reactions have resulted in considerable discomfort to the patients.

The patent literature discloses several compositions for using in treating irritation resulting from exposure to urushiols. U.S. Pat. No. 3,749,772 discloses a method of blocking the urushiols by application of a film-forming polymer and a cross-linking agent. No method of complexing the urushiols for removal from the skin is disclosed therein. U.S. Pat. No. 4,199,575 discloses a composition containing non-aqueous alkyl/aryl polyglycol ether to treat dermatitis resulting from exposure to plants of the Anacardiacea family. U.S. Pat. No. 4,451,453 discloses a method of treating skin exposed to urushiols by application of acrylic copolymer to adsorb the irritating agent. U.S. Pat. Nos. 4,861,584 and 5,017,361 disclose a method of protecting the skin from contact with allergen by application of a barrier composition containing smectite clay and quaternary ammonium compounds to absorb and block the urushiols.

From the general literature, it is suggested that compositions containing bentonite, kaolin, and silicone could be used to protect against exposure to poison ivy and poison oak dermatitis. (*Arch Dermatol*, 125, April 1989, 499-501).

The prior art inventions pose several problems. First of all, it is not effective to treat skin already exposed to urushiols with a blocking agent. The blocking agents are, furthermore, often uncomfortable and inconvenient to use.

Cyclodextrins are cyclic oligomers of glucose that are derived from starch, and that consist of rings of glucose molecules. The three most common forms, alpha-, beta-, and gamma-cyclodextrins consist, respectively, of six, seven and eight glucose molecules. The molecules contain cavities that have lipophilic properties. Cyclodextrins have been used as delivery agents for water-insoluble drugs for topical, oral and parenteral delivery. They have also been used to deliver cosmetic preparations to the skin. Cyclodextrins present an advantage as natural substances that are nontoxic and nonirritating to the skin.

U.S. Pat. No. 4,352,794 discloses and claims a method of treating acne using beta-cyclodextrin. No suggestion is made therein that the cyclodextrins have use for protection or treatment of patients that have been exposed to urushiols or that the compositions should be applied on a solid support or in form of a spray.

DETAILED DESCRIPTION OF THE INVENTION

It has now been discovered that cyclodextrins, particularly gamma-cyclodextrins, are capable of binding strongly to urushiols and can be used effectively to prevent irritation of tissue that is exposed to urushiols. In a preferred embodiment beta-hydroxypropyl-gamma-cyclodextrin is used. Compositions of the invention are basically aqueous solutions containing empty (uncomplexed) or loosely complexed cyclodextrin. It was found, surprisingly, that cyclodextrin preferentially binds urushiols even when the urushiol is dissolved in 30,000 times its weight in hexane.

Cyclodextrin-urushiol complexes can also be used to desensitize against urushiol. Compositions containing cyclodextrin/urushiol complexes may be provided as tablets for buccal administration in dosages sufficient to induce desensitizing response. In such instances, dosage is administered at desensitizing-effective levels that will cause minimal response at time of delivery or at slightly lower dosage. Compositions for desensitization may be made by the methods of the invention used to complex the urushiols from solution such as those described in Example 3. Methods of preparation of complexes of cyclodextrins are also described in U.S. Pat. No. 4,727,064, which is incorporated herein by reference. Compositions for administration for desensitization vary greatly. Most patients will be effectively treated with dosage level of 0.005 to 100 μg per dose. As is the practice in desensitization of patients, lower dosages will be administered followed by increasing dosages until desensitization levels are reached. The urushiol/cyclodextrin complexes may be tableted for administration by buccal route.

Materials and Methods:

Purified urushiols used in the examples are reference standards from the National Institutes of Health,, Center for Biologics. The standard is in the form of a 1% solution in acetone. The cyclodextrins are standard commercial materials obtainable from sources such as Sigma Chemicals (St. Louis, Mo.) and Wacker Chemicals, U.S.A. (New Canaan, Conn.).

EXAMPLE 1

Thin films of urushiols on glass microscope slides were prepared. Aliquots of urushiols in acetone (1.0 μg/μl) were spread on the ends of microscope slides and allowed to air dry. The film density was 20 μg on 4 $cm^2$. The appearance of the film was that of a thin, hazy layer, but under magnification, the layer was seen to consist of viscous microdroplets.

The prepared slides were immersed in 10% solutions of cyclodextrins in water at room temperature with very gentle stirring. The slides were removed at various times and shaken free of excess solution. Each film area was then rinsed with methanol into a quartz spectrophotometric cuvette of 1 cm path-length. The relative amount of urushiols remaining on the slides was estimated from the absorbances. Comparisons were made with control slides that were not immersed. Immersion in gamma-cyclodextrin resulted in complete removal of the urushiols within one hour. The apparent half-life for removal was about 12 minutes. Alpha- and beta-cyclodextrins were less effective for these purposes.

During immersion in the cyclodextrin solution, the urushiol film changed in appearance. The oily drops became crusty white solids. The solids eventually fell away during continued immersion. The solid complex was isolated by filtration and drying. The complex was insoluble in water and in methanol. The methanol extracts of the isolated materials were analyzed for presence of urushiol, but only trace amounts were found. This indicates that the cyclodextrin bound the urushiol firmly.

EXAMPLE 2

The process described in example 1 was repeated using hydroxypropyl-gamma-cyclodextrin. The results were similar except that the resulting complex appeared as a viscous oil rather than as a solid.

EXAMPLE 3

Ten ml of a 10% solution of gamma-cyclodextrin was placed in a vial. Ten ml of a solution of urushiol in hexane at a concentration of 10 $\mu$g/ml was layered on top of the cyclodextrin solution. (The weight ratio of hexane to urushiol was, therefore, about 33,000 to 1.) A white film of solids immediately began forming at the interface of the solutions. The mixture was stirred gently, and an aliquot of the hexane layer was periodically measured by ultraviolet spectroscopy in order to measure the percentage of the remaining urushiol. One quarter of the urushiol was extracted from the hexane solution in about 15 minutes, and in one hour about one half of the urushiol had been extracted from the hexane solution. After several hours, the white solids were removed by filtration, washed well with water and with hexane, then thoroughly air dried. The solid was found to consist of a mixture of cyclodextrin-hexane and cyclodextrin-urushiol complexes.

EXAMPLE 4

Two patients were given skin-patch titrations with varying amounts of urushiol in order to determine the minimum amount of urushiol necessary to achieve a strong allergic reaction. The reaction dosages were, in one patient, 0.05 $\mu$g and in the other 0.1 $\mu$g. These amounts were then applied to two clear areas of skin on each patient. One hour after application of the urushiols, both areas were covered with a 2×2 inch gauze pad. One pad was saturated with water and the other pad was saturated with 10% gamma-cyclodextrin in water. The areas were examined after one and two days.

Results: In both patients, the areas covered with the water gauze showed typical rash and inflammation accompanied by severe itching. The areas covered with the cyclodextrin gauze showed only a very slight rash.

The patients reported no itching in the areas that had been covered with the gauze having cyclodextrin.

The use of cyclodextrins on a support provides a particularly useful means of application and treatment of patients who have been exposed to urushiols. The cyclodextrin may be adsorbed or absorbed on the support. Supports may be, for example, a gauze sponge, cellulose such a paper, or polymeric sheets and fabrics. The supports with the cyclodextrin may be placed in air-tight packaging such as foil or plastic sheets which are sealed. For emergency facilities they may be provided in containers of multiple pre-moistened supports. The cyclodextrin compositions may also be placed in containers with dispensing means such as roll-on means, brushes, sponges, or fabrics which may placed at the container opening or be attached to the cap for easy application to affected areas. The administration of cyclodextrins using moistened supports allows targeted deliver of the cyclodextrin-containing solution. Pre-moistened sheets provide a preferred method for continued exposure of the tissue to the cyclodextrin solution.

Compositions for use in the method of the invention can also be applied as aerosols to be sprayed on the urushiol-exposed area or sprayed on supports for application to the affected area. Other methods of application include roll-on, application by hand or brush or other means. Another method of application is by immersion in or sprinkling by water containing the cyclodextrin. Suitable carriers may be in the form of powder, gel, creams pastes or suspensions. However, the carrier must not contain any component that complexes with the cyclodextrin in such a manner that it is not readily replaced by a urushiol.

Aqueous compositions are a preferred class of compositions. However, the compositions may contain alcohols or other carriers that are not firmly complexed to the cyclodextrin. The primary requirement of any composition of the invention is that the cyclodextrin either be empty of guest molecules or, if some component of the composition can be complexed, the guest molecules must be preferentially and easily displaced by urushiols. The compositions may also be provided inform of gels, lotions, and creams. However, it is crucial that the composition contain no complexed molecules that are not easily displaced by urushiols.

We claim:

1. A method of removing urushiols from a surface comprising applying to said surface a composition containing as an active agent a urushiol-complexing effective amount of cyclodextrin.

2. A method of claim 1 wherein the surface is skin.

3. A method of claim 1 wherein the cyclodextrin in the composition contains a gamma-cyclodextrin.

4. A method of claim 3 wherein the cyclodextrin is a hydroxypropyl-gamma-cyclodextrin.

5. A method of claim 1 wherein the cyclodextrin solution is on a support.

6. A method of claim 5 wherein the support is woven or matted.

7. A method of claim 5 wherein the support is a cellulose composition.

* * * * *